United States Patent [19]

Reamer et al.

[11] Patent Number: 4,719,229

[45] Date of Patent: Jan. 12, 1988

[54] ANTIHYPERCHOLESTEROLEMIC AGENTS

[75] Inventors: Robert A. Reamer, Bloomfield; Laszlo R. Treiber, Gillette, both of N.J.

[73] Assignee: Merck & Co., Inc., Rahway, N.J.

[21] Appl. No.: 49,191

[22] Filed: May 13, 1987

[51] Int. Cl.[4] .......................................... A61K 31/365
[52] U.S. Cl. .................................... 514/460; 514/529; 514/557; 514/824; 560/119; 562/501; 549/292
[58] Field of Search ............... 514/529, 557, 460, 824; 549/292; 562/501; 560/119

[56] References Cited

U.S. PATENT DOCUMENTS

| | | | |
|---|---|---|---|
| 4,231,938 | 11/1980 | Monaghan et al. | 549/292 |
| 4,387,247 | 6/1983 | Lam | 562/501 |
| 4,479,965 | 10/1984 | Terahara et al. | 514/460 |
| 4,490,546 | 12/1984 | Kuo | 549/292 |
| 4,517,373 | 5/1985 | Terahara et al. | 549/292 |
| 4,604,472 | 8/1986 | Ide et al. | 549/292 |
| 4,611,068 | 9/1986 | Guindon et al. | 549/292 |
| 4,654,363 | 3/1987 | Prugh | 514/460 |

*Primary Examiner*—James H. Reamer
*Attorney, Agent, or Firm*—Joseph F. DiPrima; Michael C. Sudol, Jr.

[57] ABSTRACT

Novel 3-hydroxy-3-methylglutaryl-coenzyme A (HMG-CoA) reductase inhibitors which are useful as antihypercholesterolemic agents are represented by the following structural formulae (I) and (II):

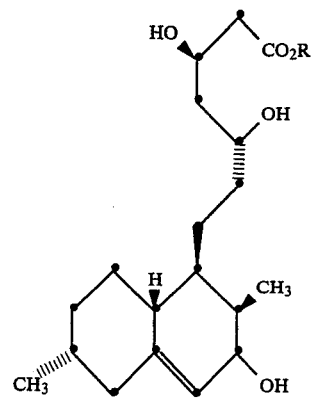

are disclosed.

7 Claims, No Drawings

ANTIHYPERCHOLESTEROLEMIC AGENTS

BACKGROUND OF THE INVENTION

Hypercholesterolemia is known to be one of the prime risk factors of cardiovascular disease, such as arteriosclerosis. To date there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof.

The naturally occurring compounds and their semi-synthetic analogs have the following general structural formulae:

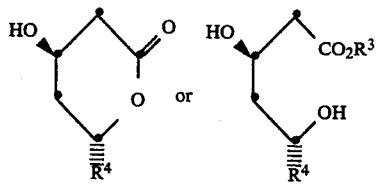

wherein:
$R^3$ is hydrogen, $C_{1-5}$ alkyl or $C_{1-5}$ alkyl substituted with a member of the group consisting of phenyl, dimethylamino, or acetylamino;
$R^4$ is:

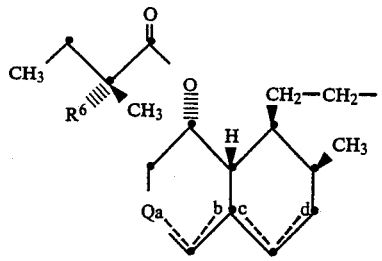

wherein
Q is

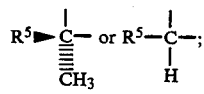

$R^5$ is H or OH;
$R^6$ is hydrogen or methyl; and
a, b, c, and d represent optional double bonds, especially where b and d represent double bonds or a, b, c, and d are all single bonds.

U.S. Pat. Nos. 4,231,938, 4,294,926 and 4,319,039 disclose the naturally occurring HMG-CoA reductase inhibitor mevinolin, and the processes for the cultivation of microorganisms of the genus Aspergillis to produce mevinolin as well as the methods utilized to isolate mevinolin from the fermentation broth.

U.S. Pat. No. 4,517,373 discloses semi-synthetic hydroxy containing compounds represented by the above general formula wherein $R^4$ is

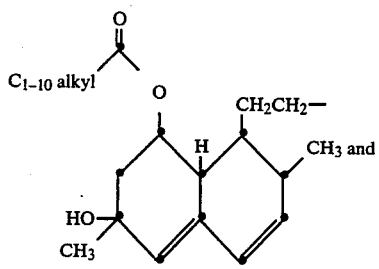

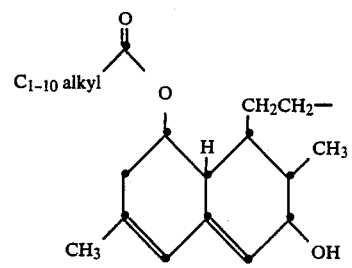

U.S. Pat. No. 4,346,227 and U.S. Pat. No. 4,448,979 also disclose semi-synthetic hydroxy-containing compounds represented by the above general formula wherein $R^4$ is

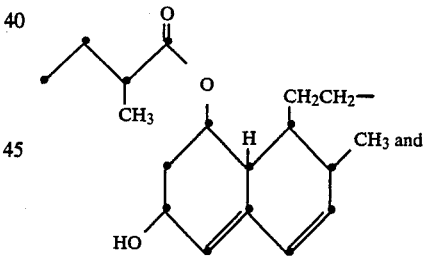

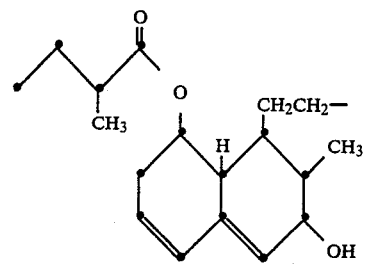

U.S. Pat. No. 4,376,863 discloses a fermentation product isolated after cultivation of a microorganism belonging to the genus Aspergillus which has a hydroxy containing butyryloxy side chain and is represented by the above general formula wherein $R^4$ is

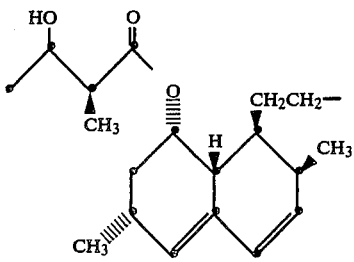

Japanese unexamined patent application No. J59-122,483-A discloses a semi-synthetic hydroxy-containing compound represented by the above general formula wherein $R^4$ is

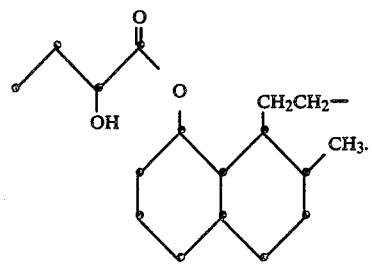

SUMMARY OF THE INVENTION

This invention relates to novel compounds which are HMG-CoA reductase inhibitors and are useful as antihypercholesterolemic agents. Specifically, the compounds of this invention are isolated after the cultivation of a microorganism belonging to the genus Aspergillis and may be biosynthetic precursors to mevinolin. Additionally, pharmaceutical compositions of these novel compounds, as a sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

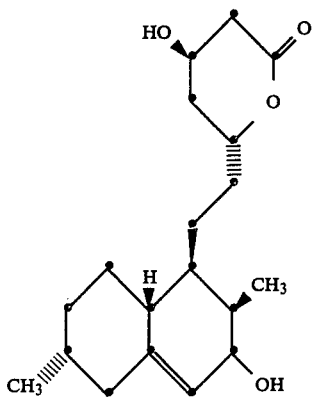

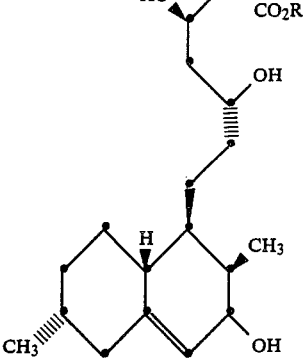

wherein: R is hydrogen, $C_{1-5}$ alkyl or $C_{1-5}$ alkyl substituted with a member of the group consisting of phenyl, dimethylamino or acetylamino; and pharmaceutically acceptable salts thereof.

It has unexpectedly been found that the cultivation of a microorganism of the genus Aspergillis which produces mevinolin also produces the compounds of the instant invention of the formula (I).

One embodiment of this invention is the compound of the formulae (I) or (II) wherein R is hydrogen. Illustrative of this embodiment is 6(R)-[2-[2(S),6(R)-dimethyl-3-hydroxy-1,2,3,5,6,7,8,8a(R)-octahydronaphthyl-1(S)ethyl]-4(R)-hydroxy-3,4,5,6-tetrahydro-2H-pyran-2-one.

Another embodiment of this invention is the class of compounds of the formula (I) wherein R is $C_{1-5}$ alkyl and pharmaceutically acceptable salts of the compounds of the formula (I) wherein R is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compound of the formula (I) is conveniently prepared by the cultivation of a microorganism of the genus Aspergillis according to the general procedures described in U.S. Pat. No. 4,231,938 and isolating the compound from the fermentation broth utilizing the concept of selective isolation involving the polarity characteristics of the compound, the in situ preparation of a phenylacyloxy derivative and chromatographic behavior of the derivative.

The compounds of the formula (I) wherein R is hydrogen or a pharmaceutically acceptable salt thereof are readily prepared by the mild basic hydrolysis of the lactone moiety of the compounds of formula (II), careful acidification and formation of the appropriate salt utilizing standard procedures.

The compounds of the formula (I) wherein R is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol described is *J. Med. Chem.*, 1985, 28, page 347.

The compound of the formula (I) wherein R is hydrogen as the potassium salt exhibited an $IC_{50}$ of 2.0 μg/ml in the above referenced protocol.

Included within the scope of this invention is the method of treating arteriosclerosis, familial hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[(S),6(R)-Dimethyl-3-hydroxy-1,2,3,5,6,7,8,8a(R)-octahydronaphthyl-1(S)]-ethyl]-4(R)-hydroxy-3,4,5,6-tetrahydro-2H-pyran-2-one A. Fermentation of Aspergillus terreus A tube of lyophilized culture MF-4845 was opened aseptically and the contents suspended in an unbaffled 250 ml Erlenmeyer flask (seed flask) containing approximately 10 ml of the Medium which has the following composition:

| Medium | |
|---|---|
| Corn steep liquor | 5 g |
| Tomato paste | 40 g |
| Oatmeal | 10 g |
| Glucose | 10 g |
| Trace Element Solution | 10 g |
| Distilled water | 1000 ml |
| pH 6.8 with NaOH | |
| Trace Element Solution: | |
| $FeSO_4.7H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6Mo_7O_{24}.4H_2O$ | 19 mg |
| $ZnSO_4.7H_2O$ | 200 mg |
| Distilled Deionized Water | 1000 ml |

The inoculated flask was incubated for 24 hours at 28° C. on a 220 rpm shaker (2 inch throw). An unbaffled 2 liter Erylenmeyer flask containing 500 ml of the medium and then inoculated with 10 ml of the first stage fermentation growth from the seed mixture. This too was shaken 24 hours at 28° C. A 200 gallon stainless steel fermentation vat was then charged with 485 liters of a medium comprising:

| | |
|---|---|
| Cerelose | 4.5% wt/vol |
| Peptonized Milk | 2.5% wt/vol |
| Autolyzed yeast | 0.25% wt/vol |
| Polyglycol P2000 | 0.25% vol/vol | whose pH was adjusted to 7.0. This was sterilized 15 minutes at 121° C. One liter of the second stage above was then charged and the mixture was incubated at 85 rpm for 12 hours then 130 rpm for 84 hours at 28° C. with an air flow of 5 cfm for 12 hours then 10 cfm for 84 hours.

B. Isolation and Purification

1. Removal of particulate matter

The supernatant of the above fermentation broth was separated from the mycelia and other solid constituents by means of any of the filtration or centrifugal methods deemed practical. In this particular example whole broth was centrifuged, and the clear supernatant was decanted. A one liter portion of the supernatant was worked up as follows:

2. Removal of solvent-extractable components

The pH of the clarified solution was adjusted to 4 with 85% phosphoric acid. The sample was extracted with 350 ml of methylene chloride. The methylene chloride phase was separated in a centrifuge and discarded. The aqueous phase was neutralized (pH 6.2) with 50% sodium hydroxide solution.

3. Extractive alkylation

The preextracted sample was mixed with 17 ml of 50% sodium hydroxide, 17 ml 85% phosphoric acid and 250 ml of 1.0M tetrabutylammonium dihydrogen-phosphate solution. The homogeneous aqueous solution was agitated with 500 ml of methylene chloride containing 3.6 g of 2-bromo-acetophenone for three hours at room temperature. The phases were separated, the aqueous phase was discarded. The organic phase was dried over anhydrous sodium sulfate and filtered. The volume of the organic phase recovered was 450 ml. The alkylation reaction was monitored by means of TLC and HPLC methods.

4. First silica gel column chromotography

Silica gel (60–200 mesh) suspended in methylene chloride was charged into a column, I.D. 3.5 cm. Bed volume and column height were 200 ml and 21 cm, respectively. The methylene chloride solution obtained in the previous step was charged onto the column. The chromatography was performed in a stepwise gradient fashion using 200 ml of each eluant in the following sequence: methylene chloride, methylene chloride-ethyl acetate in volume ratios of 9:1, 4:1, 7:3, 3:2, 1:1, 2:3, 3:7, 1:4, 1:9, and finally ethyl acetate. Eluate fractions of ca. 200 ml were collected. The chromatography was monitored by means of TLC. The bulk of the target compound was eluted with the volume ratios of 7:3 and 3:2. Fractions containing the target compound were combined and evaporated to dryness.

5. HP-20 column chromatography

Hp-20 resin was suspended in distilled water and charged into a column to form a bed with the dimensions of 70 ml in volume and 42 cm high. The dry residue obtained in the previous step was dissolved in 10 ml of acetonitrile. The column was drained to bed level, and 5 ml of the acetonitrile solution were loaded onto the column. The chromatogram was developed in a stepwise gradient mode with each increment measuring 100 ml. The gradient profile was as follows: water, water-acetonitrile 9:1, 4:1, 7:3, 3:2, 1:1, 2:3, and 3:7. The fractions collected were #1–12: 50 ml, #13–18: 20 ml each, and #19: 75 ml. The bulk of the product was found in the fractions #14–17 corresponding to a solvent ratio of 2:3. The fractions in question were combined and evaporated to dryness.

6. Second silica gel column chromatography

The dry residue obtained above was dissolved in 5 ml methylene chloride. One half of the solution (2.5 ml) was loaded onto a column of 60–200 mesh silica gel packed in hexane, and drained to bed level. The dimensions of the column were: 50 ml volume and 30 cm high. The chromatogram was developed in stepwise gradient according to the following program: 50 ml of each mixture, hexane-ethyl acetate 4:1, 3:2, 1:1, 2:3, 3:7, 1:4 and ethyl acetate. The fractions collected were 20 ml. The elution of the product started with the 1:4 mixture, and was completed with ethyl acetate corresponding to fractions #14–18. This material was sufficiently pure for NMR studies and biological tests.

C. Analytical Methodology

Analytical chromatography, TLC and HPLC, was used to monitor the isolation and purification steps.

1. Thin Layer Chromatography

Standard 20×20 cm analytical pre-coated TLC plates of type Silica Gel 60 F-254 from E. Merck were used. The chromatograms were developed in ethyl acetate in the ascending mode. The zones were located under the UV light at 254 nm as dark spots on fluorescing background. The Rf value of the phenacyloxy ester of the desired product was 0.30.

2. High Pressure Liquid Chromatography

Two gradient programs were adopted for an LC system equipped with a fast scanning diode array detector (Hewlett-Packard model 1040A):

| Solvents: | A.: | 1.01 M phosphoric acid in water |
| --- | --- | --- |
| | B.: | Acetonitrile |
| Column: | LiChrosorb RP-8 150-3 CGC column from E. Merck | |
| Conditions: | 0.7 ml/min flow rate at ambient temperature | |
| Gradient I.: | 0–15 min: | solvent B %: 50 constant |
| | 15–17 min: | solvent B %: 50 → 100, lin. grad. |
| | 17–30 min: | solvent B %: 100 constant |
| Gradient II.: | 0–2 min: | solvent B %: 40 constant |
| | 2–10 min: | solvent B %: 40 → 50, lin. grad. |
| | 10–20 min: | solvent B %: 50 → 100, lin. grad. |
| | 20–30 min: | solvent B %: 100 constant |

Retention times of the phenylacyloxy ester of the desired product was 5.6 minutes in gradient I and 11.9 minutes in gradient II.

3. Chemical Characteristics

The desired product has no distinguishing UV absorbance. However, when exposed to low pH (<5) and elevated temperatures it is converted to 7-[1,2,3,6,7,8,8a(R)-hexahydro-2(S),6(R)-dimethylnaphthyl-1(S)]-3(R),5(R)-dihydroxy heptanoic acid (Compound A) the UV spectrum and chromatographic behavior of which are well documented. The procedure for monitoring the desired compound was as follows: Samples were first assayed by LC, without any treatment, at a detector setting of 238 nm. Within the range of its stability, the desired compound was not detected as such, or indirectly as Compound A. The same sample was then acidified in aqueous solution to pH 2–3 with phosphoric acid, and agitated with toluene at 70° C. for ca. 3 hours. The toluene phase was separated and evaporated to dryness. The dry residue was redissolved in acetonitrile, and assayed by LC again. The appearance of Compound A indicated the presence of the desired compound in the original sample.

An additional method for the detection of the desired compound is described above under (B)/3. The resulting phenylacyloxy ester of the desired compound can be detected at 245 nm. Also if treated with aqueous acid/toluene as described above, it gives the phenylacyloxy ester of Compound A that can be identified by means of LC and UV spectroscopy.

4. NMR Characteristics $^1$H NMR (CD$_3$CN) δ 0.75 (3H, d, J=7.0 Hz), 0.87 (3H, d, J=7.0 Hz), 1.1–2.3 (16H, m), 2.54 (1H, d, J=6.3 Hz), 2.6 (2H, m) 3.28 (1H, d, J=3.9 Hz), 3.66 (1H, m), 3.75 (1H, m), 3.92 (1H, d, J=3.5 Hz), 4.23 (1H, m), 5.35 (1H, d of t, J=2.0, 4.3 Hz), 5.38–5.48 (2H, q, J=16.8 Hz), 7.53 (2H, m), 7.67 (1H, m), 7.94 (2H, m).

EXAMPLE 2

As a specific embodiment of a composition of this invention, 20 mg of the compound of Example 1 is formulated with sufficient finely divided lactose to provide a total amount of 580 to 590 mg to fill a size 0 hard gelatin capsule.

What is claimed is:

1. A compound represented by the following general structural formulae (I) or (II):

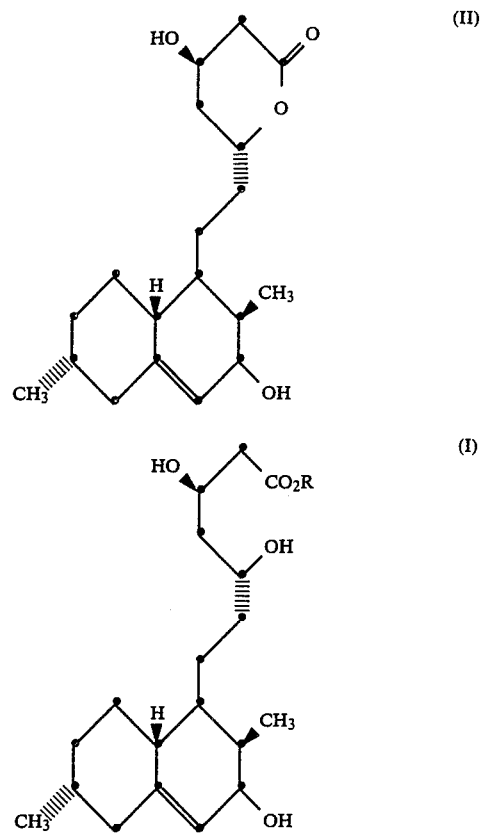

wherein R is hydrogen, C$_{1-5}$ alkyl or C$_{1-5}$ alkyl substituted with a member of the group consisting of phenyl, dimethylamino or acetylamino, or a pharmaceutically acceptable salt of the compound (I) in which R is hydrogen.

2. A compound of claim 1 wherein R is hydrogen or a pharmaceutically acceptable salt thereof.

3. A compound of claim 1 which is 6(R)-[2-[2(S),6(R)-dimethyl-3-hydroxy-1,2,3,5,6,7,8,8a-(R)]-octahydronaphthyl-1(S)]ethyl]-4(R)-hydroxy-3,4,5,6-tetrahydro-2H-pyran-2-one.

4. A hypocholesterolemic, hypolipidemic pharmaceutical composition comprising a nontoxic therapeutically effective amount of a compound of claim 1 and a pharmaceutically acceptable carrier.

5. A composition of claim 4 wherein the therapeutically active ingredient is 6(R)-[2-[2(S),6(R)-dimethyl-3-hydroxy-1,2,3,5,6,7,8,8a(R)-octahydronaphthyl-1(S)]ethyl]-4(R)-hydroxy-3,4,5,6-tetrahydro-2H-pyran-2-one.

6. A hypocholesterolimic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

7. A method of inhibiting cholesterol biosynthesis comprising the administration to a subject in need of such treatment a nontoxic therapeutically effective amount of a compound of claim 1.

* * * * *